United States Patent [19]

Fischer

[11] Plant 4,114

[45] Sept. 27, 1977

[54] AFRICAN VIOLET PLANT NAMED DOLLY

[75] Inventor: Arnold W. Fischer, Fallbrook, Calif.

[73] Assignee: Geo. J. Ball, Inc., West Chicago, Ill.

[21] Appl. No.: 730,663

[22] Filed: Oct. 7, 1976

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Rummler and Snow

[57] ABSTRACT

A new variety of African violet plant for pot plant culture distinguished by a striking blue and white bi-color flower and a profusely blooming, fast and vigorous growing plant which produces attractive light, lively green foliage.

1 Drawing Figure

BACKGROUND OF THE NEW PLANT

This new variety of African violet plant originated as a seedling of unknown parentage growing among random pollinated plants maintained at my breeding and research facilities at Hanover, Germany, in connection with my efforts to develop a unique and stable bi-color flower that would offer profuse blooming on a fast, clean growing plant. This new plant was discovered by me in 1973 and because it appeared to have the characteristics that I was seeking, it was reproduced by me by leaf cuttings from the original plant at Hanover, Germany, and then propagated through successive generations which demonstrated conclusively that the unique and distinguishing characteristics hold true from generation to generation and are firmly fixed.

Propagation of this new plant on a commercial scale is now being carried on at West Chicago, Ill., and at Woodburn, Oreg., U.S.A., by means of leaf cuttings and division of shoots and that experience with the new plant has confirmed my original observations.

DESCRIPTION OF THE DRAWINGS

My new variety of African violet is illustrated by the accompanying full color photographic drawings which in one view shows a potted plant in full bloom and in another view presents a series of typical flowers in full face display to show the color characteristics that may appear in the new plant, the color rendition being as nearly true as it is reasonably possible to obtain through conventional photographic procedures.

DESCRIPTION OF THE NEW PLANT

The following is a detailed description of my new variety of African violet plant based upon observations of greenhouse plants at West Chicago, Ill., and with color designations according to the R.H.S. Colour Chart published by The Royal Horticultural Society of London, England.

THE PLANT

Origin: Seedling.
Parentage: Unknown.
Classification:
*Botanic.—Saintpaulia ionantha.*
*Commercial.*—African violet pot plant.
Form: Compact potted plant.
Height: 3 to 4 inches from soil to top of flower; 1 to 2 inches from soil to top of plant.

Growth: Condensed and moderately vigorous with fairly strong, horizontally spreading petioles.
Foliage: Quantity — abundant.
Number of leaves: Variable.
Size of leaves: 2½ to 3½ inches long, 2 to 3 inches wide in mature leaf.
Shape of leaves: Orbicular with a sagittate base, an acute to obtuse apex, and crenate margins tending toward being serrate.
Texture: Velutinous.
Venation: Pinnately veined, pronounced on under side of leaves.
Color:
*Upper side.*—Green 137B-C.
*Under side.*—Greyed Green 193B-C.
Petioles: 2 to 3½ inches long.

THE BUD

Form: Globular, becoming urn shaped as it opens.
Size: ¼ inch in diameter just before opening.
Opening rate: Bud opens slowly, 2 to 4 weeks from visible bud to open flower.
Color:
*When sepals first divide.*—Yellow Green 145D
*When sepals begin to unfurl.*—Yellow Green 145D. center with Violet Blue 90A margin.
Sepals: Hooded over bud for a short period.
*Form.*—Spear-shaped and upstanding.
*Curlback.*—Slightly but appressed to petals.
*Size.*—1/32 to 1/16 inch wide and 3/16 inch long.
*Color.*—Inside — Green 143C. Outside — Green 143C.
Calyx: Synsepalous and funnel shaped.
*Size.*—⅜ to ½ inch wide.
*Splitting.*—Calyx splits to star shape.
*Aspect.*—Inside — smooth. Outside — hairy.
Preduncle: Length — 1 to 1¾ inches, average 1⅜ inches.
*Strength.*—Strong and erect.
*Aspect.*—Velutinous.
*Color.*—Yellow Green 145B.

THE FLOWER

Blooming habit: Recurrent to continuous the year around with more flowers in spring and fall than in other periods.
Size of flower: Medium to large.
*Diameter.*—1 to 2 inches, averaging 1½ inches.

*Depth.*—$\frac{3}{8}$ to $\frac{1}{2}$ inch becoming more flattened as it opens.

Shape of flower: Cup-shaped when bloom first opens becoming flattened when fully opened.

Borne: The inflorescence is a cyme.

Petalage:

*Number of petals.*—5 with petaloid anthers when single; 10 to 13 when fully double and also with petaloid anthers.

*Arrangement.*—Gamopetalous.

*Form.*—Rotate with petals having slightly wavy margins, zygomorphic when single.

*Texture.*—Soft.

*Appearance.*—Glittery on upper side and satiny on under side.

*Color.*—Upper side of petals — Violet Blue 90B at edges merging with an inner band of 90D about 1/8 to 3/16 inch wide, the center portion being White 155C. Reverse side — Margin Violet Blue 90B to 90D with White 155C center.

Petaloids: One or two petaloid anthers on single flowers, one to four on double flowers.

*Size.*—$\frac{1}{4}$ to $\frac{3}{8}$ inch.

*Color.*—Same as the petals.

Peduncle: Upright — $1\frac{1}{2}$ to $2\frac{1}{2}$ inches long.

*Pedicels.*—$\frac{7}{8}$ to $1\frac{1}{4}$ inches long.

*Color.*—Yellow Green 145B.

Discoloration after full bloom: None.

Persistence: Flowers hang on and at senescence turn brown.

Effect of weather: Hot weather decreases the life of the flowers and causes the color to be less intense. The plants thrive in 70 to 80% relative humidity.

Lasting quality: 10 to 14 days for the fully opened flowers.

REPRODUCTIVE ORGANS

Stamens:

*Anthers.*—2 when single, each with 2 anther cells, and 4 when double, each with 2 anther cells. Arrangement: Basifixed and connate at apex. Filaments: $\frac{1}{8}$ to 3/16 inch long. Color: White 155A. Pollen: Color — Yellow 7A.

*Pistils.*—Number — one. Style: 5/16 to $\frac{3}{8}$ inch long. Color: Green at base, white medially, and Violet 88B at apex. Stigma: Color — Violet 88B.

*Ovaries.*—Superior and velutinous.

*Fruit.*—Normally none seen, except where special attempts have been made to pollinate the flower.

This new variety of African violet plant is particularly characterized by its profuse blooming habit and production of striking bi-colored flowers. The plant is a very fast and vigorous grower and produces attractive lively green foliage, the ease of growth being very notable. The coloring of the blooms is affected by cultural practices such as fertility and light but the blooms always display a strong bi-color characteristic.

I claim:

1. A new and distinct cultivar of African violet substantially as herein shown and described, characterized by its medium to large blue and white bi-colored blossoms, its very fast and vigorous growth habit, and its profuse year around blooming capability.

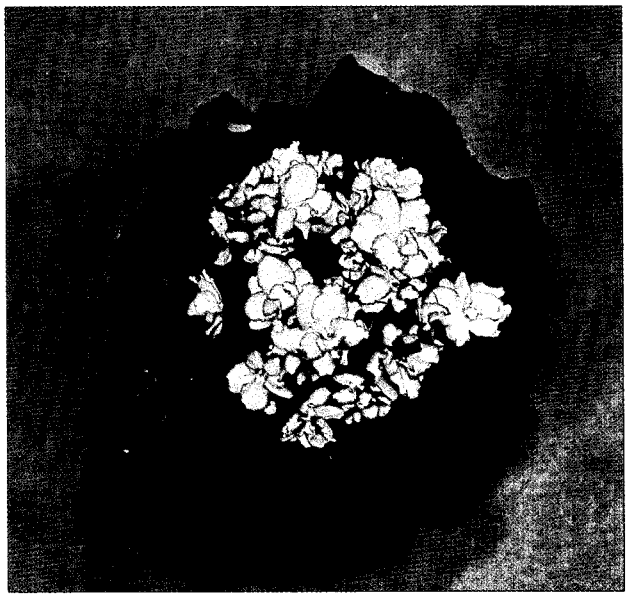
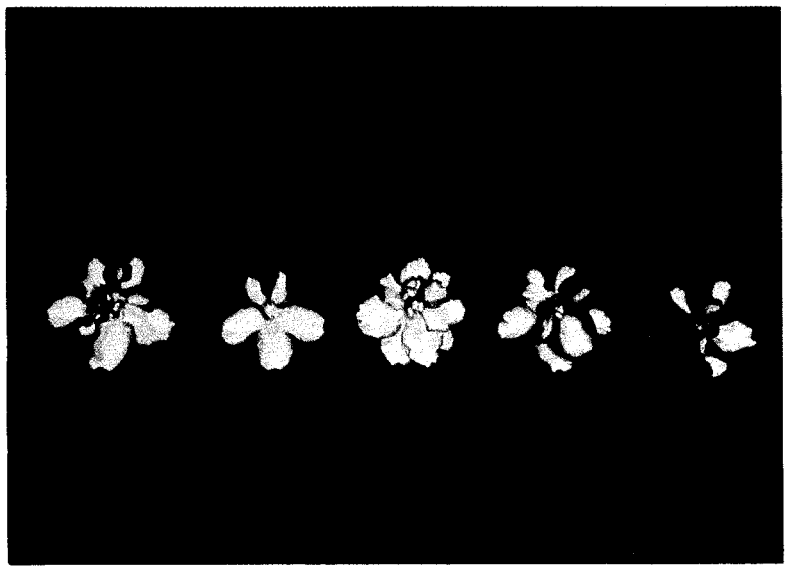

* * * * *